(12) United States Patent
Goodrich et al.

(10) Patent No.: US 7,648,699 B2
(45) Date of Patent: *Jan. 19, 2010

(54) PREVENTING TRANSFUSION RELATED COMPLICATIONS IN A RECIPIENT OF A BLOOD TRANSFUSION

(75) Inventors: Raymond P. Goodrich, Lakewood, CO (US); Junzhi Li, Arvada, CO (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/469,186

(22) Filed: Aug. 31, 2006

(65) Prior Publication Data

US 2007/0098697 A1 May 3, 2007

Related U.S. Application Data

(63) Continuation-in-part of application No. 10/648,536, filed on Aug. 25, 2003, which is a continuation of application No. 10/377,524, filed on Feb. 28, 2003, which is a continuation of application No. 09/586,147, filed on Jun. 2, 2000, now abandoned.

(60) Provisional application No. 60/714,682, filed on Sep. 7, 2005.

(51) Int. Cl.
  *C12N 5/00* (2006.01)
  *A01N 1/02* (2006.01)
  *C12N 13/00* (2006.01)
  *C12N 5/08* (2006.01)

(52) U.S. Cl. .................. 424/93.7; 435/2; 435/173.1; 435/173.3; 435/363; 435/366; 435/372; 435/325; 424/93.72

(58) Field of Classification Search .................. None
See application file for complete search history.

(56) References Cited

U.S. PATENT DOCUMENTS

| | | |
|---|---|---|
| 683,690 A | 10/1901 | Johnson |
| 1,733,239 A | 10/1929 | Roberts |
| 1,961,700 A | 6/1934 | Moehler |
| 2,056,614 A | 10/1936 | Moehler |
| 2,212,330 A | 8/1940 | Thomas |
| 2,340,890 A | 2/1944 | Lang et al. |
| 2,417,143 A | 3/1947 | Tishler et al. |
| 2,786,014 A | 3/1957 | Tullis |
| 3,057,865 A | 10/1962 | Bardos et al. |
| 3,456,053 A | 7/1969 | Crawford |
| 3,629,071 A | 12/1971 | Sekhar |
| 3,683,177 A | 8/1972 | Veloz |
| 3,683,183 A | 8/1972 | Vizzini et al. |
| 3,705,985 A | 12/1972 | Manning et al. |
| 3,776,694 A | 12/1973 | Leittl |
| 3,852,032 A | 12/1974 | Urbach |
| 3,864,081 A | 2/1975 | Logrippo |
| 3,874,384 A | 4/1975 | Deindoerfer et al. |
| 3,894,236 A | 7/1975 | Hazelrigg |
| 3,926,556 A | 12/1975 | Boucher |
| 3,927,325 A | 12/1975 | Hungate et al. |
| 4,061,537 A | 12/1977 | Seiler et al. |
| 4,112,070 A | 9/1978 | Harmening |
| 4,124,598 A | 11/1978 | Hearst et al. |
| 4,139,348 A | 2/1979 | Swartz |
| 4,159,320 A | 6/1979 | Opitz |
| 4,169,204 A | 9/1979 | Hearst et al. |
| 4,173,631 A | 11/1979 | Graham et al. |
| 4,181,128 A | 1/1980 | Swartz |
| 4,196,281 A | 4/1980 | Hearst et al. |
| 4,264,601 A | 4/1981 | Trachewsky |
| 4,267,269 A | 5/1981 | Grode et al. |
| 4,312,883 A | 1/1982 | Baccichetti et al. |
| 4,321,918 A | 3/1982 | Clark, II |
| 4,321,919 A | 3/1982 | Edelson |
| 4,336,809 A | 6/1982 | Clark |
| 4,381,004 A | 4/1983 | Babb |

(Continued)

FOREIGN PATENT DOCUMENTS

EP  0066886  8/1982

(Continued)

OTHER PUBLICATIONS

Hiroshi et al. Transplantation, vol. 84(9), Nov. 15, 2007, pp. 1174-1182.*

(Continued)

*Primary Examiner*—Rebecca E Prouty
*Assistant Examiner*—Jae W Lee
(74) *Attorney, Agent, or Firm*—Laura B. Arciniegas; Edna M. O'Connor; John R. Merkling

(57) ABSTRACT

This invention is directed toward a process for reducing transfusion related complications in a recipient of an allogeneic blood transfusion by adding to the blood to be transfused a photosensitizer comprising riboflavin, irradiating the blood and riboflavin with light, transfusing the irradiated blood into a recipient, and reducing a transfusion related complication by the recipient to cells in the donor blood. The invention is also directed towards a process for preventing rejection of a donor organ by a recipient comprising the steps of transfusing the recipient of the donor organ with treated platelets; and transplanting the donor organ into the recipient.

9 Claims, 5 Drawing Sheets

U.S. PATENT DOCUMENTS

| | | |
|---|---|---|
| 4,390,619 A | 6/1983 | Harmening-Pittiglio |
| 4,398,031 A | 8/1983 | Bender et al. |
| 4,398,906 A | 8/1983 | Edelson |
| 4,402,318 A | 9/1983 | Swartz |
| 4,407,282 A | 10/1983 | Swartz |
| 4,421,987 A | 12/1983 | Herold |
| 4,424,201 A | 1/1984 | Valinsky et al. |
| 4,428,744 A | 1/1984 | Edelson |
| 4,432,750 A | 2/1984 | Estep |
| 4,456,512 A | 6/1984 | Bieler et al. |
| 4,457,918 A | 7/1984 | Holick et al. |
| 4,464,166 A | 8/1984 | Edelson |
| 4,467,206 A | 8/1984 | Taylor et al. |
| 4,474,153 A | 10/1984 | Hanamoto |
| 4,481,167 A | 11/1984 | Ginter et al. |
| 4,493,981 A | 1/1985 | Payne |
| 4,568,328 A | 2/1986 | King |
| 4,572,899 A | 2/1986 | Walker et al. |
| 4,573,960 A | 3/1986 | Goss |
| 4,573,961 A | 3/1986 | King |
| 4,573,962 A | 3/1986 | Troutner |
| 4,576,143 A | 3/1986 | Clark, III |
| 4,578,056 A | 3/1986 | King et al. |
| 4,585,735 A | 4/1986 | Meryman et al. |
| 4,596,547 A | 6/1986 | Troutner |
| 4,604,356 A | 8/1986 | Blake, II |
| 4,608,255 A | 8/1986 | Kahn et al. |
| 4,609,372 A | 9/1986 | Carmen et al. |
| 4,612,007 A | 9/1986 | Edelson |
| 4,613,322 A | 9/1986 | Edelson |
| 4,614,190 A | 9/1986 | Stanco et al. |
| 4,623,328 A | 11/1986 | Hartranft |
| 4,626,431 A | 12/1986 | Batchelor et al. |
| 4,642,171 A | 2/1987 | Sekine et al. |
| 4,645,649 A | 2/1987 | Nagao |
| 4,648,992 A | 3/1987 | Graf et al. |
| 4,649,151 A | 3/1987 | Dougherty et al. |
| 4,651,739 A | 3/1987 | Oseroff et al. |
| 4,675,185 A | 6/1987 | Kandler et al. |
| 4,683,195 A | 7/1987 | Mullis et al. |
| 4,683,202 A | 7/1987 | Mullis |
| 4,683,889 A | 8/1987 | Edelson |
| 4,684,521 A | 8/1987 | Edelson |
| 4,693,981 A | 9/1987 | Wiesehahn et al. |
| 4,695,460 A | 9/1987 | Holme |
| 4,704,352 A | 11/1987 | Miripol et al. |
| 4,708,715 A | 11/1987 | Troutner et al. |
| 4,726,949 A | 2/1988 | Miripol et al. |
| 4,727,027 A | 2/1988 | Wiesehahn et al. |
| 4,737,140 A | 4/1988 | Lee et al. |
| 4,748,120 A | 5/1988 | Wiesehahn |
| 4,769,318 A | 9/1988 | Hamasaki et al. |
| 4,775,625 A | 10/1988 | Sieber |
| 4,784,852 A | 11/1988 | Johansson |
| 4,788,038 A | 11/1988 | Matsunaga |
| RE32,874 E | 2/1989 | Rock et al. |
| 4,828,976 A | 5/1989 | Murphy |
| 4,831,268 A | 5/1989 | Fisch et al. |
| 4,833,165 A | 5/1989 | Louderback |
| 4,861,704 A | 8/1989 | Reemtsma et al. |
| 4,866,282 A | 9/1989 | Miripol et al. |
| 4,878,891 A | 11/1989 | Judy et al. |
| 4,880,788 A | 11/1989 | Moake et al. |
| 4,915,683 A | 4/1990 | Sieber |
| 4,921,473 A | 5/1990 | Lee et al. |
| 4,925,665 A | 5/1990 | Murphy |
| 4,930,516 A | 6/1990 | Alfano et al. |
| 4,946,438 A | 8/1990 | Reemtsma et al. |
| 4,948,980 A | 8/1990 | Wedekamp |
| 4,950,665 A | 8/1990 | Floyd |
| 4,952,812 A | 8/1990 | Miripol et al. |
| 4,960,408 A | 10/1990 | Klainer et al. |
| 4,961,928 A | 10/1990 | Holme et al. |
| 4,978,688 A | 12/1990 | Louderback |
| 4,986,628 A | 1/1991 | Lozhenko et al. |
| 4,992,363 A | 2/1991 | Murphy |
| 4,994,367 A | 2/1991 | Bode et al. |
| 4,998,931 A | 3/1991 | Slichter et al. |
| 4,999,375 A | 3/1991 | Bachynsky et al. |
| 5,011,695 A | 4/1991 | Dichtelmuller et al. |
| 5,017,338 A | 5/1991 | Surgenor |
| 5,020,995 A | 6/1991 | Levy |
| 5,030,200 A | 7/1991 | Judy et al. |
| 5,039,483 A | 8/1991 | Sieber et al. |
| 5,041,078 A | 8/1991 | Matthews et al. |
| 5,089,146 A | 2/1992 | Carmen et al. |
| 5,089,384 A | 2/1992 | Hale |
| 5,092,773 A | 3/1992 | Levy |
| 5,114,670 A | 5/1992 | Duffey |
| 5,114,957 A | 5/1992 | Hendler et al. |
| 5,120,649 A | 6/1992 | Horowitz et al. |
| 5,123,902 A | 6/1992 | Muller et al. |
| 5,133,932 A | 7/1992 | Gunn et al. |
| 5,147,776 A | 9/1992 | Koerner, Jr. |
| 5,149,718 A | 9/1992 | Meruelo et al. |
| 5,150,705 A | 9/1992 | Stinson |
| 5,166,528 A | 11/1992 | Le Vay |
| 5,184,020 A | 2/1993 | Hearst et al. |
| 5,185,532 A | 2/1993 | Zabsky et al. |
| 5,192,264 A | 3/1993 | Fossel |
| 5,211,960 A | 5/1993 | Babior |
| 5,216,251 A | 6/1993 | Matschke |
| 5,229,081 A | 7/1993 | Suda |
| 5,232,844 A | 8/1993 | Horowitz et al. |
| 5,234,808 A | 8/1993 | Murphy |
| 5,236,716 A | 8/1993 | Carmen et al. |
| 5,247,178 A | 9/1993 | Ury et al. |
| 5,248,506 A | 9/1993 | Holme et al. |
| 5,250,303 A | 10/1993 | Meryman et al. |
| 5,258,124 A | 11/1993 | Bolton et al. |
| 5,269,946 A | 12/1993 | Goldhaber et al. |
| 5,273,713 A | 12/1993 | Levy |
| 5,281,392 A | 1/1994 | Rubinstein |
| 5,288,605 A | 2/1994 | Lin et al. |
| 5,288,647 A | 2/1994 | Zimlich, Jr. et al. |
| 5,290,221 A | 3/1994 | Wolf, Jr. et al. |
| 5,300,019 A | 4/1994 | Bischof et al. |
| 5,304,113 A | 4/1994 | Sieber et al. |
| 5,318,023 A | 6/1994 | Vari et al. |
| 5,340,716 A | 8/1994 | Ullman et al. |
| 5,342,752 A | 8/1994 | Platz et al. |
| 5,344,752 A | 9/1994 | Murphy |
| 5,344,918 A | 9/1994 | Dazey et al. |
| 5,358,844 A | 10/1994 | Stossel et al. |
| 5,360,734 A | 11/1994 | Chapman et al. |
| 5,366,440 A | 11/1994 | Fossel |
| 5,372,929 A | 12/1994 | Cimino et al. |
| 5,376,524 A | 12/1994 | Murphy et al. |
| 5,378,601 A | 1/1995 | Gepner-Puszkin |
| 5,399,719 A | 3/1995 | Wollowitz et al. |
| 5,418,130 A | 5/1995 | Platz et al. |
| 5,419,759 A | 5/1995 | Naficy |
| 5,427,695 A | 6/1995 | Brown |
| 5,433,738 A | 7/1995 | Stinson |
| 5,459,030 A | 10/1995 | Lin et al. |
| 5,466,573 A | 11/1995 | Murphy et al. |
| 5,474,891 A | 12/1995 | Murphy |
| 5,482,828 A | 1/1996 | Lin et al. |
| 5,487,971 A | 1/1996 | Holme et al. |
| 5,494,590 A | 2/1996 | Smith et al. |
| 5,503,721 A | 4/1996 | Hearst et al. |
| 5,512,187 A | 4/1996 | Buchholz et al. |
| 5,516,629 A | 5/1996 | Park et al. |
| 5,527,704 A | 6/1996 | Wolf, Jr. et al. |

| Patent No. | Date | Inventor |
|---|---|---|
| 5,536,238 A | 7/1996 | Bischof |
| 5,545,516 A | 8/1996 | Wagner |
| 5,547,635 A | 8/1996 | Duthie, Jr. |
| 5,550,111 A | 8/1996 | Suhadolnik et al. |
| 5,556,958 A | 9/1996 | Carroll et al. |
| 5,556,993 A | 9/1996 | Wollowitz et al. |
| 5,557,098 A | 9/1996 | D'Silva |
| 5,559,250 A | 9/1996 | Cook et al. |
| 5,569,579 A | 10/1996 | Murphy |
| 5,571,666 A | 11/1996 | Floyd et al. |
| 5,578,736 A | 11/1996 | Wollowitz et al. |
| 5,585,503 A | 12/1996 | Wollowitz et al. |
| 5,587,490 A | 12/1996 | Goodrich, Jr. et al. |
| 5,593,823 A | 1/1997 | Wollowitz et al. |
| 5,597,722 A | 1/1997 | Chapman et al. |
| 5,607,924 A | 3/1997 | Magda et al. |
| 5,618,662 A | 4/1997 | Lin et al. |
| 5,622,867 A | 4/1997 | Livesey et al. |
| 5,624,435 A | 4/1997 | Furumoto et al. |
| 5,624,794 A | 4/1997 | Bitensky et al. |
| 5,625,079 A | 4/1997 | Wollowitz et al. |
| 5,628,727 A | 5/1997 | Hakky et al. |
| 5,639,376 A | 6/1997 | Lee et al. |
| 5,639,382 A | 6/1997 | Brown |
| 5,643,334 A | 7/1997 | Eckhouse et al. |
| 5,652,096 A | 7/1997 | Cimino |
| 5,653,887 A | 8/1997 | Wahl et al. |
| 5,654,443 A | 8/1997 | Wollowitz et al. |
| 5,656,154 A | 8/1997 | Meryman |
| 5,656,498 A | 8/1997 | Iijima et al. |
| 5,658,530 A | 8/1997 | Dunn |
| 5,658,722 A | 8/1997 | Margolis-Nunno et al. |
| 5,683,661 A | 11/1997 | Hearst et al. |
| 5,683,768 A | 11/1997 | Shang et al. |
| 5,686,436 A | 11/1997 | Van Dyke |
| 5,688,475 A | 11/1997 | Duthie, Jr. |
| 5,691,132 A | 11/1997 | Wollowitz et al. |
| 5,698,524 A | 12/1997 | Mach et al. |
| 5,698,677 A | 12/1997 | Eibl et al. |
| 5,702,684 A | 12/1997 | McCoy et al. |
| 5,707,401 A | 1/1998 | Talmore |
| 5,709,653 A | 1/1998 | Leone |
| 5,709,991 A | 1/1998 | Lin et al. |
| 5,709,992 A | 1/1998 | Rubinstein |
| 5,712,085 A | 1/1998 | Wollowitz et al. |
| 5,712,086 A | 1/1998 | Horowitz et al. |
| 5,714,328 A | 2/1998 | Magda et al. |
| 5,736,313 A | 4/1998 | Spargo et al. |
| 5,739,013 A | 4/1998 | Budowsky et al. |
| 5,753,428 A | 5/1998 | Yuasa et al. |
| 5,756,553 A | 5/1998 | Iguchi et al. |
| 5,769,839 A | 6/1998 | Carmen et al. |
| 5,772,960 A | 6/1998 | Ito et al. |
| 5,783,093 A | 7/1998 | Holme |
| 5,789,150 A | 8/1998 | Margolis-Nunno et al. |
| 5,789,151 A | 8/1998 | Bitensky et al. |
| 5,789,601 A | 8/1998 | Park et al. |
| 5,798,238 A | 8/1998 | Goodrich, Jr. et al. |
| 5,798,523 A | 8/1998 | Villeneuve et al. |
| 5,817,519 A | 10/1998 | Zelmanovic et al. |
| 5,827,644 A | 10/1998 | Floyd et al. |
| 5,834,198 A | 11/1998 | Famulok et al. |
| 5,840,252 A | 11/1998 | Giertych |
| 5,843,459 A | 12/1998 | Wang et al. |
| 5,846,961 A | 12/1998 | Van Dyke |
| 5,854,967 A | 12/1998 | Hearst et al. |
| 5,866,074 A | 2/1999 | Chapman et al. |
| 5,869,701 A | 2/1999 | Park et al. |
| 5,871,900 A | 2/1999 | Wollowitz et al. |
| 5,876,676 A | 3/1999 | Stossel et al. |
| 5,899,874 A | 5/1999 | Jonsson |
| 5,906,915 A | 5/1999 | Payrat et al. |
| 5,908,742 A | 6/1999 | Lin et al. |
| 5,919,614 A | 7/1999 | Livesey et al. |
| 5,922,278 A | 7/1999 | Chapman et al. |
| 5,935,092 A | 8/1999 | Sun et al. |
| 5,955,256 A | 9/1999 | Sowemimo-Coker et al. |
| 5,955,257 A | 9/1999 | Burger et al. |
| 5,965,349 A | 10/1999 | Lin et al. |
| 5,972,593 A | 10/1999 | Wollowitz et al. |
| 5,976,884 A | 11/1999 | Chapman et al. |
| 5,981,163 A | 11/1999 | Horowitz et al. |
| 6,004,741 A | 12/1999 | Wollowitz et al. |
| 6,004,742 A | 12/1999 | Wollowitz et al. |
| 6,017,691 A | 1/2000 | Wollowitz et al. |
| 6,020,333 A | 2/2000 | Berque |
| 6,060,233 A | 5/2000 | Wiggins |
| 6,063,624 A | 5/2000 | Kandler et al. |
| 6,077,659 A | 6/2000 | Ben-Hur et al. |
| 6,087,141 A | 7/2000 | Margolis-Nunno et al. |
| 6,093,725 A | 7/2000 | Cook et al. |
| 6,106,773 A | 8/2000 | Miekka et al. |
| 6,133,460 A | 10/2000 | Wollowitz et al. |
| 6,143,490 A | 11/2000 | Cook et al. |
| 6,171,777 B1 | 1/2001 | Cook et al. |
| 6,177,441 B1 | 1/2001 | Cook et al. |
| 6,194,139 B1 | 2/2001 | Wollowitz et al. |
| 6,197,207 B1 | 3/2001 | Chapman et al. |
| 6,214,534 B1 | 4/2001 | Horowitz et al. |
| 6,218,100 B1 | 4/2001 | Wollowitz et al. |
| 6,258,319 B1 | 7/2001 | Hearst et al. |
| 6,258,577 B1 | 7/2001 | Goodrich et al. |
| 6,268,120 B1 | 7/2001 | Platz et al. |
| 6,270,952 B1 | 8/2001 | Cook et al. |
| 6,277,337 B1 | 8/2001 | Goodrich et al. |
| 6,410,219 B1 | 6/2002 | Cook et al. |
| 6,413,714 B1 | 7/2002 | Margolis-Nunno et al. |
| 6,420,570 B1 | 7/2002 | Wollowitz et al. |
| 6,433,343 B1 | 8/2002 | Cimino et al. |
| 6,455,286 B1 | 9/2002 | Wollowitz et al. |
| 6,461,567 B1 | 10/2002 | Hearst et al. |
| 6,469,052 B2 | 10/2002 | Wollowitz et al. |
| 6,503,699 B1 | 1/2003 | Wollowitz et al. |
| 6,514,987 B1 | 2/2003 | Cook et al. |
| 6,544,727 B1 | 4/2003 | Hei |
| 6,565,802 B1 | 5/2003 | Hanley et al. |
| 6,576,201 B1 | 6/2003 | Woo et al. |
| 6,586,749 B2 | 7/2003 | Cimino et al. |
| 6,596,230 B1 | 7/2003 | Woo et al. |
| 6,680,025 B2 | 1/2004 | Hearst et al. |
| 6,686,480 B2 | 2/2004 | Wollowitz et al. |
| 2001/0053547 A1 | 12/2001 | Slichter |
| 2002/0022215 A1 | 2/2002 | Sobsey et al. |

FOREIGN PATENT DOCUMENTS

| | | |
|---|---|---|
| EP | 0124363 | 4/1984 |
| EP | 0108588 | 5/1984 |
| EP | 0196515 | 3/1986 |
| EP | 0184331 | 11/1986 |
| EP | 0491757 | 8/1990 |
| EP | 0525 138 | 12/1991 |
| EP | 0590514 | 4/1994 |
| EP | 0679398 | 2/1995 |
| EP | 0510185 | 11/1996 |
| EP | 0754461 | 1/1997 |
| EP | 0801072 | 10/1997 |
| FR | 2674753 | 9/1992 |
| FR | 2715303 | 7/1995 |
| FR | 2718353 | 10/1995 |
| GB | 2034463 | 6/1980 |
| JP | 59020218 | 2/1984 |
| WO | WO83/02328 | 7/1983 |
| WO | WO88/02116 | 5/1985 |
| WO | WO88/10087 | 12/1988 |
| WO | WO89/06702 | 7/1989 |

| | | |
|---|---|---|
| WO | WO90/00059 | 1/1990 |
| WO | WO90/10461 | 9/1990 |
| WO | WO91/02529 | 7/1991 |
| WO | WO92/08348 | 5/1992 |
| WO | WO92/08349 | 5/1992 |
| WO | WO92/11057 | 9/1992 |
| WO | WO92/17173 | 9/1992 |
| WO | WO93/00005 | 7/1993 |
| WO | WO94/07426 | 4/1994 |
| WO | WO94/07499 | 4/1994 |
| WO | WO95/02325 | 1/1995 |
| WO | WO95/11028 | 4/1995 |
| WO | WO95/12973 | 5/1995 |
| WO | WO95/16348 | 6/1995 |
| WO | WO96/14740 | 5/1996 |
| WO | WO96/14741 | 5/1996 |
| WO | WO97/07674 | 3/1997 |
| WO | WO97/18844 | 5/1997 |
| WO | WO97/22245 | 6/1997 |
| WO | WO97/36581 | 9/1997 |
| WO | WO97/36634 | 9/1997 |
| WO | WO98/22150 | 5/1998 |
| WO | WO98/30545 | 7/1998 |
| WO | WO98/31219 | 7/1998 |
| WO | WO98/41087 | 9/1998 |
| WO | WO98/51147 | 11/1998 |
| WO | WO99/11305 | 11/1999 |
| WO | WO00/04930 | 2/2000 |
| WO | WO00/11946 | 9/2000 |
| WO | WO01/28599 | 4/2001 |
| WO | WO02/02153 | 1/2002 |
| WO | WO02/30190 | 4/2002 |

OTHER PUBLICATIONS

Corash et al. (Novel processes for inactivation of leukocytes to prevent transfusion associated graft-versus-host disease, Bone Marrow Transplantation (2004) 33, 1-7).*

Abdursashidova et al, "Polynucleotide-protein interactions in the translation system. Identification of proteins interacting with tRNA in the A- and P-sites of *E. Coli* ribosomes," 1979 *Nucleic Acids Res.* 6(12):3891-3909.

Belikov et al, "Choice of an Effective Method of Analysis of Riboflavin and Stud of its Stability", DrugU, AN 1988, 37(2), Suppl. S26, 1988-39621.

Benade et al, "Inactivation of free and cell-associated human immunodeficiency virus in platelet suspensions by aminomethyltrimethylpsoralen and ultraviolet light", *Transfusion*, vol. 34, No. 8, 1994, pp. 680-684.

Blundell et al, "A prospective, randomized study of the use of platelet concentrates irradiated with ultraviolet-B light in patients with hematologic malignancy", *Transfusion*, 1996; 36:296-302.

Brodie et al, "Mode of Action of Vitamin K in Microorganisms," 1966, *Vitam. Horm* 24:447-463.

Budowsky et al, "Induction of polynucleotide-protein cross-linkages by ultraviolet irradiation," 1986, *Eur. J. Biochem.* 159:95-101.

Budowsky et al, "Polynucleotide-Protein Cross-Links Induced by Ultraviolet Light and Their Use for Structural Investigation of Nucleoproteins," 1989, *Progress in Nucleic Acid Res. And Mol. Bio* 37:1-65.

Budowsky et al, "Preparation of cyclic 2',3'-monophosphates of oligoadenylates (A2'p)nA>p and A3'p(A2'p)n-1A>, p," 1994, *Eur. J. Biochem.* 220:97-104.

Budowsky et al, "Principles of selective inactivation of viral genome. VIII, The influence of β-propiolactone on immunogenic and protective activities of influenza virus," 1993, *Vaccine* 11(3):343-348.

Budowsky et al, "Principles of selective inactivation of viral genome. VI, Inactivation of the infectivity of the influenza virus by the action of β-propiolactone,", 1991, *Vaccine* 9:398-402.

Budowsky et al, "Principles of selective inactivation of viral genome. VII, Some peculiarities in determination of viral suspension infectivity during inactivation by chemical agents,", 1991, *Vaccine* 9:473-476.

Budowsky, EI, "Problems and Prospects for Preparation of Killed Antiviral Vaccines", 1991, *Adv. Virus Res.* 39:255-290.

Cadet et al., "Mechanisms and Products of Photosensitized Degradation of Nucleic Acids and Related Model Compounds," 1983, *Israel J. Chem.* 23:420-429.

Capon et al, "Effective Ultraviolet Irradiation of Platelet Concentrates in Teflon Bags", *Transfusion*, 1990; 30:678-681.

Chow et al., "Recognition of G-U mismatches by tris(47-diphenyl-110-phenanthroline)rhodium(III)," 1992 *Biochemistry* 31(24):5423-5429.

Clarke, H., "A photodecomosition fluorimetric method for determination of riboflavin in the various constituents of blood", *Int. J. Vit. Nutr. Res.*, 1977, 47(4):356-360.

Communication pursuant to Article 96(2) EPC from corresponding EP Application 03 751 901.4—1219, dated Oct. 20, 2006.

Corash et al, "Use of 8-Methoxypsoralen and long wavelength ultraviolet radiation for decontamination of platelet concentrates", *Blood Cells*, 1992, 18:57-74.

Corash, L; "Inactivation of Viruses, Bacteria, Protozoa, and Leukocytes in Platelet Concentrates", *Vox Sanguinis*, 1998; 74 (suppl. 2): 173-176.

Deutsch, E. "Vitamin K in Medical Practice: Adults," 1966, *Vitam. Horm.*, 24:665-680.

Dodd et al, "Inactivation of Viruses in platelet suspensions that retain their in vitro characteristics: comparison of psoralen-ultraviolet A and merocyanine 540-visible light methods", *Transfusion*, vol. 31, No. 6, 1991, pp. 483-490.

Dodd, RY, "Viral inactivation in platelet concentrates", *TCB*, 1994, 3:181-186.

Ennever et al, "Short Communication Photochemical Reactions of Riboflavin: Covalent Binding to DNA and to Poly (dA) Poly (dT)," 1983 *Pediatr. Res.* 17:234-236.

Fast et al, "Functional inactivation of white blood cells by Mirasol treatment", *transfusion*, 2006; 46:642-648.

Fast et al, "Inhibition of xenogeneic GVHD by PEN110 treatment of donor human PBMNCs", *Transfusion*, 2004; 44:282-285.

Fast et al, "PEN110 treatment functionally inactivates the PBMNCs present in RBC units: comparison to the effects of exposure to gamma irradiation", *Transfusion*, 2002; 42:1318-1325.

Friedman et al, "Reducing the Infectivity of Blood Components — What we have learned", 1995, *Immunological Investigations* 24 1&2: 49-71.

Gasparro, F.P., "Symposium-in-Print: Psoralen Photobiology: Recent Advances", *Photochemistry and Photobiology*, 1996, 63(5):553-557.

Ghiron et al, "The Flavin-sensitized Photoinactivation of Trypsin," 1965, *Photochemistry and Photobiology* 4:13-26.

Goodrich et al, "The design and development of selective, photoactivated drugs for sterilization of blood products," 1997, *Drugs of the Future* 22(2):159-171.

Grana et al, "Use of 8-methoxypsoralen and Ultraviolet-A Pretreated Platelet Concentrates to Prevent Alloimmunication Against Class I Major Histocompatibility Antigens", *Blood*, 1991; 77:2530-2537.

Grijzenhout et al, "UVB Irradiation of Human Platelet Concentrates does not Prevent HLA Alloimmunization in Recipients", *Blood*, 1994, No. 10, pp. 3524-3531.

Hanchett et al, "Development of a Simple, Clinically Applicable Closed-System for the Photochemical Treatment of Peripheral Blood Mononuclear Cells (PBMC) for Allogeneic Cell Immune Therapy", present at 42nd Annual Meeting of the American Society of hematology, 2000, abstract., www.cerus.com.

Hanson, C.V., "Photochemical Inactivation of Viruses with Psoralens: An Overview", *Blood Cells*, 1992, 18:7-25.

Hanson, CV, "Photochemical Inactivation of Deoxyribonucleic and Ribonucleic Acid Viruses by Chlorpromazine", *Antimicrob. Agent Chemother.*, 1979, 15(3), pp. 461-464.

Hei et al, "Elimination of cytokine production in stored platelet concentrate aliquots by photochemical treatment with psoralen plus ultraviolet A light", *Transfusion*, vol. 39, 1999, pp. 239-248.

Heinmets et al, "Inactivation of Viruses in Plasma by Photosensitized Oxidation", Walter Reed Army Institute of Research, Nov. 1955, pp. 1-16.

Hoffmann et al "DNA Strand Breaks in mammalian Cells Exposed to Light in the Presence of Riboflavin and Tryptophan," *Photochemistry and Photobiology*, vol. 29 pp. 299-303 (1979).

International Search Report for PCT/US99/16404.

Isaacs et al, "Synthesis and Characterization of New Psoralen Derivatives with Superior Photoreactivity with DNA and RNA", *Biochemistry*, vol. 16, No. 6, 1977, pp. 1058-1064.

Ivanchenko et al, "The photochemistry of purine components of nucleic acids. I. The efficiency of photolysis of adenine and guanine derivatives in aqueous solution,", 1974, *Nucleic Acids Res.* 2(8):1365-1373.

Johnson et al, "Photochemical Treatment of Donor Lymphocytes Inhibited Their Ability to Facilitate Donor Engraftment or Increase Donor Chimerism after Nonmyeloablative Conditioning or Establishment of Mixed Chimerism", *Bio of Blood and Marrow Transplantation*, 2002, 8:581-587.

Joshi, P.C., "Comparison of the DNA-damaging property of photosensitized riboflavin via singlet oxygen (1O2) and superoxide radical (Oi) mechanisms," (1985) *Toxicology Letters* 26:211-217.

Kabuta et al. (1978), "Inactivation of viruses by dyes and visible light," *Chem. Abstracts* 87(1), Abstract No. 400626.

Kale et al. (1992), "Assesment of the genotoxic potential of riboflavin and lumiflavin; B. Effect of light," *Mutation Res.* 298:17-23.

Klebanoff et al, "The risk of Childhood Cancer after Neonatal Exposure ot Vitamin K," 1993, *New Eng. J. Med*, 329(13):905-908.

Kobayashi et al. (1983), "The molecular mechanism of mutation. Photodynamic action of flavins on the RNA-synthesizing system," *Chem. Abstracts* 98(1), Abstract No. 1200.

Korycka et al, "Photodegradation of DNA with fluorescent light in the presence of riboflavin, and photoprotection by flavin triplet-state quenchers," (1980) *Biochimica et Biophysica Acta* 610:229-234.

Kovalsky et al, "Laser (Two-Quantum) Photolysis of Polynucleotides and Nucleoproteins: Quantitative Processing of Results," 1990 *Photochemistry and Photobiology* 5(6):659-665.

Kuratomi et al, "Studies on the Interactions Between DNA and Flavins," (1977) *Biochemica et Biophysica Acts* 476:207-217.

Leontis et al, "The 5SrRNA loop E: Chemical probing and phylogenetic data versus crystal structure", 1998, *RNA* 4:1134-1153.

Lim et al, "Chemical probing of tDNAPhewith transition metal complexes: a structural comparison of RNA and DNA," 1993, *Biochemistry* 32:11029-11034.

Lin et al, "Use of 8-Methoxypsoralen and Long-Wavelength Ultraviolet Radiation for Decontamination of Platelet Concentrates", *Blood*, vol. 74, No. 1, 1989, pp. 517-525.

Maddox, J., "The working of vitamin K," (1991) *Nature* 353(6346):695.

Maksimovich et al, "Content of basal water-soluble vitamins and of carotene in stored donor blood", *Probl. Gemtol I Pereliv Krovi*, 1962, 792);40-44, abstract only.

Malik et al, "New Trends in Photobiology—Bactericidal Effects of Photoactivated Porhyrins—an Alternative Approach to Antimicrobial Drugs," *J. Photochem. Photobiol* Pt.B: Biology, 1990, V:281-293.

Matsuki et al, "Acceleration of methaemoglobin reduction by riboflavin in human erthrocytes", *Br. J. Haematology*, 1978, 39(4):523-528.

Matthews et al., "Photodynamic therapy of viral contaminants with potential for blood banking applications," (1988) *Transfusion* 28(1):81-83.

McCord, EF, "Chemically induced dynamic nuclear polarization studies of yeast", 1984, *Biochemistry* 23:1935-1939.

Merenstein et al, (Vitamin K ad Hoc Task Force), "Controversies concerning vitamin K and the newborn," 1993, *Pediatrics* 901(5):1001-1005

Merrifield et al, Vitamin K as a fungistatic agent, 1965, *Appl. Microbio.* 13(5):660-662.

Merrifield et al, "Factors affecting the antimicrobial acitivity of Vitamin K5," 1965, *Appl. Microbio.* 13(5):766-770.

Moroff et al, "Factors Influencing Virus Inactivation and Retention of Platelet Properties Following Treatment with Aminomethyltrimethylpsoralen and Ultraviolet A Light", *Blood Cells*, 1992, 18:43-56.

Murata et al., "Effect of vitamins other than vitamin C on viruses: virus-inactivating activity of vitamin K5" (1983) *J. Nutr. Sci. Vitaminol* (Tokyo) 29(6):721-724.

Naseem et al., "Effect of alkylated and intercalated DNA on the generation of superoxide anion by riboflavin," (1988) *Bioscience Reports* 8(5):485-492.

Neyndorff et al., "Development Of A Model To Demonstrate Photosensitizer-mediated Viral Inactivation in Blood," Quadra Logic Technologies, Inc., and the Department of Microbiology, U. of British Columbia, 1990, pp. 485-490.

North et al, "Photosensitizers as Virucidal Agents", *J. Photochem. Photobiol.*, 1993, 17(2), pp. 99-108.

Peak et al., "DNA Breakage Caused by 334-nm Ultraviolet Light is Enhanced by Naturally Occurring Nucleic Acid Components and Nucleotide Coenzymes," 1984 *Photochemistry and Photobiology* 39(5):713-716.

Piette et al., "Alteration of Guanine Residues During Proflavine Mediated Photosensitization of DNA," (1981) *Photochemistry and Photobiology* 33:325-333.

Piette et al., "Production of Breaks in Single- and Double-Stranded Forms of Bacteriophage X174 DNA by Proflavine and Light Treatment," (1979) *Photochemistry and Photobiology* 30:369-378.

Pratt et al, "Vitamin K5 as an Antimicrobial Medicament and Preseravative", 1950, *J. Am. Pharm. Assn* 39(3):127-134.

Prodouz et al, "Effects of Two Viral Inactivation Methods on Platelets: Laser-UV Radiation and Merocyanine 540-Mediated Photoinactivation", *Blood Cells*, 1992, 18:101-116.

Prodouz et al, "Inhibition by albumin of merocyanine 540-mediated photosensitization of platelets and viruses", *Transfusion*, vol. 31, No. 3, 1991, pp. 415-422.

Purmal et al, "Removal of White Blood Cell and Plasma Proteins from Leukofiltered RBC Concentrates by Inactine Pathogen Inactivation Process", American Association of Blood Banks Meeting, Oct. 2001, Poster.

Racek et al, "Influence of antioxidants on the quality of stored blood", *Vox Sanguinis*, 1997, 72(1):16-19.

Ramu et al, "The Riboflavin-Mediated Photoxidation of Oxorubicin" *Cancer Chemother. Pharmacol*, 2000, 46(6), 449-458.

Reinhardt et al, "Virucidal activity of retinal", *Antimicrobial Agents and Chemotherapy* 16:3, Sep. 1979, p. 421-423.

Schwartzman, G., "Antibacterial Properties of 4-Amino-2-Methyl-1-Naphthol Hydrocloride," 1948, Proc. *Soc. Exp. Biol. Med.* 67:376-378.

Simukova et al, "Conversion of Non-covalent Interactions in Nucleoproteins into Covalent Bonds: UV-Induced Formation of Polynucleotide-Protein Crosslinks in Bacteriophage Sd Virions," 1974, *FEVS Letters* 38(3):299-303.

Slichter et al, "Prevention of platelet alloimmunization in dogs with systemic cyclosporine and by UV-irradiation or cyclosporine-loading of donor platelets", *Blood*, 1987; 69:414-418.

Slichter et al, "Trial to Reduce Alloimmunization to Platelets Study Group. Leukocyte Reduction and Ultraviolet B irradiation of Platelets to Prevent Alloimmunization and Refractoriness to Platelet Transfusions", *NEJM*, 1997; 337:1861-1869.

Snyder, "Storage of platelet concentrates after high-dose ultraviolet B irradiation", *Transfusion*, 1991; 31:491-496.

Speck et al., "Further Observations on the Photooxidation of DNA in the Presence of Riboflavin," (1976) *Biochimica et Biphysica Acta* 435:39-44.

Spranger, J. "Does vitamin K cause cancer?" 1993, *Eur. J. Pediatr.* 152(2):174.

Stassinopoulos et al, "Helinx Technology, Utilized in the Intercept Blood System, Effectively Inactivates *Deinoccus radiodurans*, a Bacterium with Highly Efficient DNA Repair", Abstract presented at the 44th Annual Meeting of the American Society of Hematology, 2002, *Blood* 100(11)(part 2 of 2): p. 708a, 2002, Abstract #2790.

Tandy et al, "Platelet Transfusions Irradiated with Ultraviolet-B light may have a Role in Reducing Recipient Alloimmunization", *Blood Coagul Fibrinolysis*, 1991; 2:383-388.

Truitt et al, "Photochemical Treatment with S-59 Psoralen and Ultraviolet A light to Control the Fate of Naive or Primed T Lymphocytes In Vivo, after Allogeneic Bone Marrow Transplantation", *J. Immunology*, 1999, 163:5145-5156.

Tsugita. et al., "Photosensitized inactivation of ribonucleic acids in the presence of riboflavin," (1965) *Biochim. Biophys. Acta* 103:360-363.

Uehara et al, "Effect of adenine on the riboflavin-sensitized photoreaction. II. Effect of adenine on the photodynamic inactivation of transforming deoxyribonucleic acid in the presence of riboflavin", 1972, *J Biochemistry*, 71:5, 805-810.

Uehara et al, "Effect of adenine on the riboflavin-sensitized photoreaction. I. Effect of adenine on the photodynamic inactivation of yeast alcohol dehydrogenase in the presence of riboflavin,"*J. Vitaminology*, 17:3,1971,148-154.

Van Marwijk Kooy et al, "Irradiation of platelets with UV-B light exposes fibrinogen binding sites via an intracellular mechanism", *Br. J. Haematol.*, 1990; 76:531-536.

Van Prooijen et al, "Evaluation of a new UVB source for irradiation of platelet concentrates", , *Br. J. Haematol*, 1990; 75:573-577.

Vest, M., "Vitamin K in medical practice; pediatrics," 1966, *Vitami. Horm.* 24:649-663.

Webb et al, "Mutagenesis in Escherichia coli by Visible Light," 1967, *Science* 156:1104-1105.

Yang et al, "Vitamin K5 as a Food Preservative," *1958 Food Technology* 501-504.

* cited by examiner

PREVENTING TRANSFUSION RELATED COMPLICATIONS IN A RECIPIENT OF A BLOOD TRANSFUSION

PRIORITY CLAIM

This invention claims the benefit of U.S. provisional application No. 60/714,682 filed Sep. 7, 2005. This instant application is a continuation-in-part of U.S. patent application Ser. No. 10/648,536, filed Aug. 25, 2003, which is a continuation of Ser. No. 10/377,524 filed Feb. 28, 2003, which is a continuation of Ser. No. 09/586,147, filed Jun. 2, 2000, now abandoned.

FIELD OF THE INVENTION

This invention is directed to methods of preventing transfusion related complications in a recipient of allogeneic donor blood.

BACKGROUND

Whole blood collected from volunteer donors for transfusion into recipients is typically separated into components: red blood cells, white blood cells, platelets, plasma and plasma proteins, using apheresis or other known methods. Each of these separated blood components may be stored individually for later use and are used to treat a multiplicity of specific conditions and disease states. For example, the red blood cell component is used to treat anemia, the concentrated platelet component is used to control bleeding, and the plasma protein component is used frequently as a source of Clotting Factor VIII for the treatment of hemophilia.

In cell separation procedures, there is unusually some small percentage of other types of cells which are carried over into a separated blood component. When contaminating cells are carried over into a separated component of cells in a high enough percentage to cause some undesired effect, the contaminating cells are considered to be undesirable. White blood cells, which may transmit infections such as HIV and CMV also cause other transfusion-related complications such as transfusion-associated Graft vs. Host Disease (TA-GVHD), alloimmunization and microchimerism.

TA-GVHD is a disease produced by the reaction of immunocompetent T lymphocytes of the donor that are histoincompatible with the cells of the recipient into which they have been transplanted. Recipients develop skin rashes, fever, diarrhea, weight loss, hepatosplenomegaly and aplasia of the bone marrow. The donor lymphocytes infiltrate the skin, gastrointestinal tract and liver. Three weeks following transfusion 84% of patients who develop TA-GVHD die.

Alloimmunization describes an immune response provoked in a recipient by an alloantigen from a donor of the same species. Alloantigens include blood group substances (A, B, O) on erythrocytes and histocompatibility antigens.

Chimerism, or microchimerism refers to the small numbers of donor cells found in the recipient's body outside the region of the organ transplant. It is believed that the presence of these cells may contribute to the long term development of autoimmune diseases in the transfusion recipient.

Human Leukocyte Antigen (HLA) markers are found on the cell membranes of many different cell types, including white blood cells. HLA is the major histocompatibility complex (MHC I) in humans, and contributes to the recognition of self v. non-self. Recognition by a transfusion recipient's immune system of differences in HLA antigens on the surface of the transfused cells may be the first step in the rejection of transplanted tissues. Therefore, the phenomena of alloimmunization of recipients against HLA markers on donor blood is a major problem in transfusion medicine today. This issue arises in recipients of blood products due to the generation of antibodies against white blood cell HLA antigens in donor blood by the recipient.

Platelets also contain low levels of these HLA antigens because they bud from a megakaryocyte cell (a form of white cell) located primarily in the bone marrow. When a recipient of a whole blood or blood component transfusion generates antibodies against the HLA antigens on the white blood cells of the donor blood cells, a consequence is that these antibodies also lead to recognition and clearance of platelets that carry this same marker. When this occurs, it becomes necessary to HLA match the donor and recipient in order to assure that the recipient receiving the transfusion is able to maintain an adequate number of platelets in circulation. This is often a complicated, expensive and difficult procedure but a necessary one, since rapid clearance of the platelets due to antibody-antigen interaction would otherwise put the recipient at severe risk of bleeding to death. In cases where recipients are very heavily transfused with blood or blood products from multiple donors and antibodies to several different HLA markers are generated, or where no suitable matched donor for platelets is available, death frequently results for those patients who become alloimmunized and sustain a bleed.

Since the problem arises from the presence of white cells in the donated blood products, the elimination of white cells from these products would be expected to reduce the likelihood and frequency of reactions. Gamma irradiation of blood products, which kills the cells but does not remove them from the blood product to be transfused, has not been shown to be able to prevent alloimmunization reactions. It is likely that this is due to the fact that the treated cells are still present and capable of presenting antigens to the recipient's immune system.

Filtration of white blood cells from blood or blood products to be transfused has been shown to be capable of reducing alloimmunization reactions. This has been demonstrated based on an extensive clinical study known as the TRAP study. It was conducted as a multi-institutional study between 1995-1997 and results were subsequently published in the NEJM in 1997 (Trial to Reduce Alloimmunization to Platelets Study Group. Leukocyte reduction and ultraviolet B irradiation of platelets to prevent alloimmunization and refractoriness to platelet transfusions. N Engl J Med. 1997;337:1861-1869). The data from that study suggested that leukoreduction significantly decreased the likelihood of alloimmunization reactions in patients from 13% for non-leukoreduced, untreated products to 3-5% for leukoreduced products. As a result of this work, platelet products have been routinely filtered by a variety of methods to remove WBC. The remaining levels of alloimmunization that were observed were believed to be due to residual white blood cells that were not filtered out. Even the best WBC filters cannot remove 100% of the white blood cells and those left behind are potentially able to stimulate antibody production against the HLA markers on the remaining cells. A decrease in the occurrence rate from 13% of patients receiving platelets to 3-4% is significant, but still leaves several tens of thousands of cases occurring on an annual basis.

In the same TRAP study, treatment of platelet products with ultraviolet B (UVB) light was evaluated. In the case of the UVB treatment, the results were equivalent to those obtained through leukoreduction. The work was consistent with prior studies that showed that UVB treated platelet products possessed significantly reduced alloimmunization responses (Blundell et al. Transfusion 1996; 36: 296-302).

This was believed to be due to changes in white cells induced by UVB that cause them to present their antigens and have those antigens processed differently from non-irradiated cells by the patient's immune system. The result is that antibody generation is significantly suppressed for UVB treated products. Although the results were positive, the UVB treatment described in the TRAP study was not adopted widely, because the UV dose required to suppress the alloimmunization response damaged the platelets to an extent which did not allow the platelets to be stored with adequate maintenance of their efficacy (Grijzenhout et al. Blood 1994; 84: 3524-3531).

Photosensitizers, or compounds which absorb light of a defined wavelength and transfer the absorbed energy to an electron acceptor may be a solution to the above problems, by inactivating undesirable cells contaminating a blood product without damaging the desirable components of blood.

There are many photosensitizer compounds known in the art to be useful for inactivating undesirable cells and/or other infectious particles. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, anthroquinones and endogenous photosensitizers.

As described above, ways to reduce the risks of transfusion related complications from white blood cells is either to reduce the number of white blood cells transfused into a recipient to an extent that no immune response is generated, and/or to effectively destroy the viability and capacity of any transfused white blood cells to function post transfusion.

What is not known is whether donor cells which have been subjected to pathogen reduction treatment with riboflavin and light have modified HLA surface markers, and therefore will not cause transfusion related complications such as alloimmunization, GVHD and microchimerism in the recipient.

It is to this second aspect that this invention is directed.

SUMMARY OF THE INVENTION

This invention is directed toward a process for reducing transfusion related complications in a recipient of an allogeneic blood transfusion by adding to the blood to be transfused a photosensitizer comprising riboflavin, irradiating the blood and riboflavin with light, transfusing the irradiated blood into a recipient, and reducing a transfusion related complication by the recipient to cells in the donor blood.

Also claimed is a blood product for transfusion into a recipient comprising inactivated blood or a blood product which has been treated with riboflavin and light. The treated blood or blood product will not cause transfusion related complications in the recipient when transfused.

The invention is also directed towards a process for preventing rejection of a donor organ by a recipient comprising the steps of transfusing the recipient of the donor organ with treated platelets; and transplanting the donor organ into the recipient.

DETAILED DESCRIPTION

Photosensitizers useful in this invention include endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. When endogenous photosensitizers are used, particularly when such photosensitizers are not inherently toxic or do not yield toxic photoproducts after photoradiation, no removal or purification step is required after decontamination, and the decontaminated product can be directly administered to a recipient in need of its therapeutic effect.

Examples of such endogenous photosensitizers which may be used in this invention are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavin adenine dinucleotide [FAD]) and alloxazine mononucleotide (also known as flavin mononucleotide [FMN] and riboflavine-5-phosphate). The term "alloxazine" includes isoalloxazines.

Use of endogenous isoalloxazines as a photosensitizer to pathogen reduce blood and blood components are described in U.S. Pat. Nos. 6,258,577 and 6,277,337 both issued to Goodrich et al., and are herein incorporated by reference to the amount not inconsistent.

Figure 1:
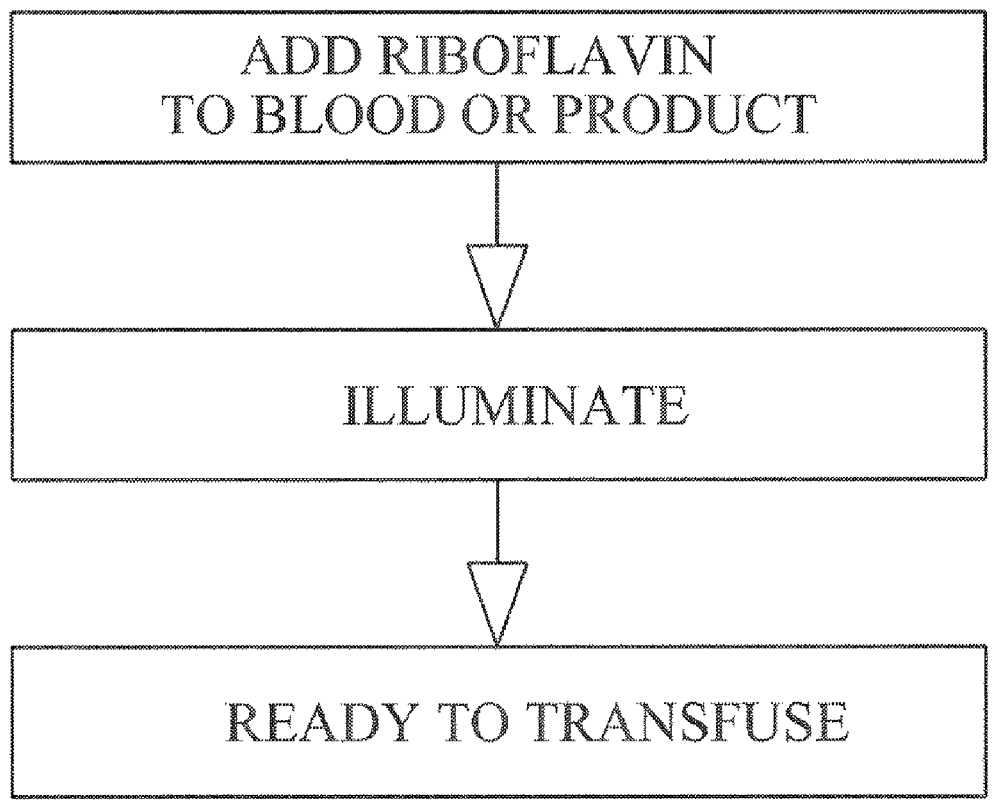
FIG. 1 depicts an embodiment of the invention to treat donor cells to be transfused into a recipient with riboflavin and light.

The process of using endogenous alloxazine and light to reduce the risks of transfusion related complications from contaminating white blood cells in blood or blood products are shown in FIG. 1.

Whole blood to be transfused into a recipient is collected from a donor. If desired, the whole blood may be separated into blood components using any available procedures and/or extracorporeal blood processing machines. 50 µM riboflavin in PBS is added to the whole blood or separated blood components. The blood product and riboflavin are illuminated at a wavelength of between about 290-370 nm for a sufficient amount of time to reduce the number of white blood cells present in the donor blood or blood product to an extent that no immune response to the donor blood is generated by the transfusion recipient, and/or to effectively destroy the viability and capacity of any transfused donor white blood cells to function in the recipient post transfusion. An illumination time of around 8 minutes appears to be satisfactory. The inactivated blood product is ready to be transfused into a donor.

The following examples show that allogeneic and xenogeneic donor cells subjected to a pathogen reduction treatment with riboflavin and light will not cause transfusion related complications in a donor such as alloimmunization, TA-GVHD and microchimerism.

EXAMPLE 1

The intent of this study was to determine whether human peripheral blood mononuclear cells (PBMNCs) treated with riboflavin and light (hereinafter known as treated cells) could be induced to proliferate in vitro when exposed to a growth stimulus, or whether the treated cells were rendered inactive by the treatment, and therefore could not be induced to proliferate. Untreated cells (control) are those human PBMNCs not treated with riboflavin and light.

For this study, PBMNC were obtained from three human donors, with each donor set being split into a treated and untreated subset. Each subset was subsequently tested using the in vitro test methods described below. PBMNC were isolated from platelets obtained from the donors using a standard apheresis procedure on a Trima® apheresis machine (available from Gambro BCT, Lakewood, Colo., USA). For treatment with riboflavin and light, the cells were added to ABO-matched platelet-poor plasma (PPP), which was then mixed with riboflavin and illuminated according to the procedure shown in FIG. 1.

CD3 is the signaling complex of the T lymphocyte cell receptor. Anti-CD3$^+$ antibody has been shown to induce proliferation of T cells. CD28 is a low affinity T cell receptor that interacts with B7 (ligand for CD28). CD28 is considered a co-stimulatory receptor because its signals are synergistic with those provided by the CD3 receptor in promoting T cell activation and proliferation. Signals from CD28 to the CD3 receptor also increase the synthesis of many cytokines. Cytokines are produced primarily by lymphocytes in response to a stimulus. Production of cytokines is therefore a measure of white blood cell health.

Preparation of CD3, CD3/CD28 or Control Coated Plates

PBS containing 10 μg/mL of anti-CD3 (NA/LE, Pharmingen), 10 μg/mL anti-CD3 and 4 μg/mL anti-CD28 (NA/LE, Pharmingen) or PBS alone were added to wells (50 μl per well) in a 96 well flat bottom plate. The plates were incubated for at least 90 minutes at room temperature. Following 2 washes of the wells with PBS, 100 μl of RPMI 1640 media containing 5% human AB serum, penicillin and streptomycin was added to all wells and the plates were incubated at room temperature for at least another 60 minutes. Then 100 μl of the treated or untreated cells at 2×10$^6$ cells/ml in RPMI 1640 containing 5% human AB serum, penicillin and streptomycin were added to the wells (replicate 6 wells per group).

1. A. The effect of treatment with riboflavin and light on the ability of PBMNC to proliferate in response to CD3 and CD3/CD28 stimulation.

Figure 2:
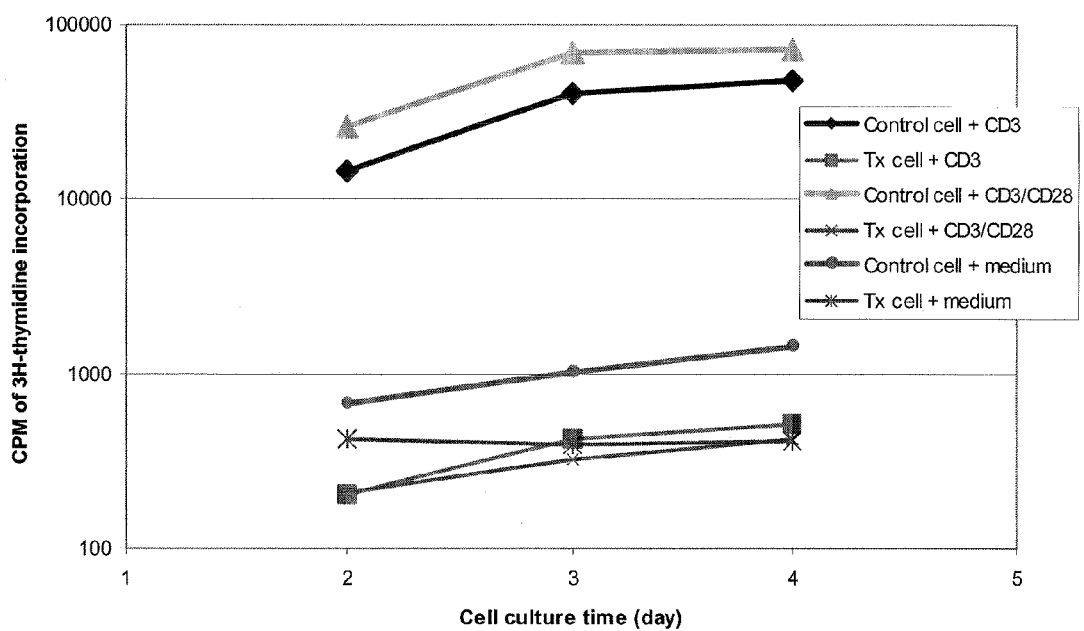
FIG. 2 is a graph showing the effect of treatment with riboflavin and light on the ability of peripheral blood mononuclear cells (PBMNC) to proliferate in response to CD3 and CD3/CD28 stimulation.

As shown in FIG. 2, anti-CD3 antibody induced significant proliferation of untreated (designated as Control cell+CD3 in FIG. 2) cells in all 3 donors. The combination of anti-CD3 and anti-CD28 antibodies further increased proliferation of untreated (Control cell+CD3/CD28) cells. Both treated (designated as Tx+medium in FIG. 2) and untreated (Control cell+medium) cells present in media alone exhibited minimal proliferation. In contrast, the treated PBMNCs did not proliferate in response to either anti-CD3 (Tx cell+CD3) or anti-CD3/CD28 antibody (Tx cell+CD3/CD28) stimulus.

1. B. The Ability of the Treated or Untreated PBMNC to Produce Cytokines

Figure 3:
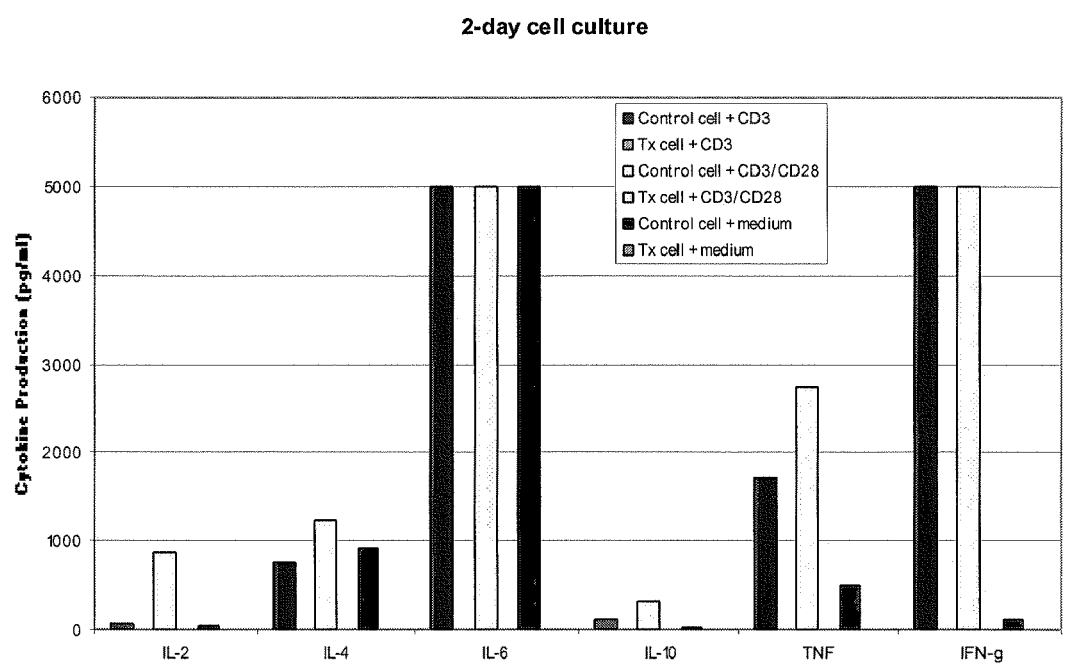
FIG. 3 is a graph comparing the production of cytokines by treated and untreated PBMNC.

A comparison of the levels of cytokines present in the supernatants of the wells after 2 days in culture indicated that both anti-CD3 antibody (Control cell+CD3) and anti-CD3/CD28 antibodies (Control cell+CD3/CD28) induced increased cytokine production by the untreated PBMNCs. As shown in FIG. 3, higher levels of some cytokines could be detected in the wells containing control cells and medium alone (Control cell+medium). However, the treated cells (Tx cell+CD3; Tx+CD3/CD28 or Tx cell+medium) did not produce cytokines in any of the wells, even in the media control.

This data demonstrates that the treated leukocytes are unresponsive in that they do not exhibit any significant proliferation or cytokine production.

EXAMPLE 2

2. A. The Ability of Treated or Untreated PBMNC to be Activated in Response to PMA Phorbol myristic acetate (PMA) is a stimulus that activates WBCs but does not cause proliferation. One of the results of this activation signal is the upregulation onto the surface of the leukocyte the activation antigen CD69. Activation through CD69 does not cause the cell to proliferate. This assay determined whether treatment with riboflavin and light interferes with the ability of the cells to be activated.

As above, WBC were obtained from the leukocyte reduction chamber of a Trima® machine following a double unit platelet collection. The peripheral blood mononuclear cells (PBMNCs) were purified by Ficoll-Hypaque discontinuous gradient centrifugation. These PBMNCs were divided into 2 aliquots and one aliquot was placed in an Extended Life Platelet (ELP) bag containing autologous human plasma and exposed to riboflavin and light. Following the treatment, the PBMNC were collected by centrifugation, washed and then placed in a 50 ml tube filled with RPMI 1640 containing 10% fetal calf serum (FCS). The cells were initially counted and then the following assays were performed:

Stock PMA (Sigma) at 0.5 mg/ml in DMSO was diluted to 1000 ng/ml in PBS. 50 μL of PMA or PBS was transferred to 12×75 mm tubes. Treated and untreated PBMNC were adjusted to 1×10$^6$/ml in RPMI-10% Fetal calf serum (R10 medium) and 450 μL of each was transferred to tubes containing either 50 μL of PMA or PBS. The tubes were incubated in a 37° C. water bath for 4 hours. 50 μL of cells were stained with 20 μL of CD8FITC, CD69PE, and CD3PerCP (Becton Dickinson, Fast Immune Kit) and analyzed on the FACScan Flow Cytometer (Becton Dickinson). Fluorescence of the cells containing CD69 and CD8 fluorescent markers was acquired by gating on the CD3$^+$ PerCP positive cells, and quadrant analysis used to assess the level of lymphocyte activation.

The results are shown in Table 2A below. Summarizing this data shows that untreated (−) CD3$^+$ cells (both CD4$^+$ (helper T cells) and CD8$^+$ (cytotoxic T cells)) expressed CD69 upon activation with PMA, while the treated (+) CD3$^+$ cells (both CD4+ and CD8$^+$) did not express CD69 upon activation with PMA. Thus treatment with riboflavin and light resulted in almost 100% inhibition of the ability of PMA to activate cells.

TABLE 2A

| Experiment No. | Treatment | % CD3$^+$ CD4$^+$ CD69$^+$ cells | % CD3$^+$ CD8$^+$ CD69$^+$ cells |
| --- | --- | --- | --- |
| 1 | − | 39.7 | 7.7 |
| 1 | + | 0.5 | 0.0 |
| 2 | − | 62.9 | 11.3 |
| 2 | + | 2.8 | 0.3 |
| 3 | − | 59.5 | 15.1 |
| 3 | + | 1.2 | 0.2 |

2. B. The Effect of Treatment on the Ability of PBMNC to Proliferate in Response to Mitogens and Allogenenic Stimulator Cells Other stimuli that have been shown to induce PBMNC to proliferate are mitogens such as phytohemagglutinin (PHA), which activates T lymphocytes (CD8$^-$), and allogeneic stimulator PBMNC. Allogenic stimulator cells are cells from a different donor which initiates an immune response by presenting antigen to responder cells. The ability of treated or untreated PBMNC to proliferate in response to these stimuli was tested. Responder cells proliferate in response to antigen presentation by a stimulator cell.

To measure the proliferative response to PHA, PBMNC were adjusted to $1\times10^6$/ml in RPMI-10% fetal calf serum, and Phytohemagglutinin-M(PHA-M) (Gibco) was diluted 1:40 in R10 medium. Equal volumes (100 uL) of each were transferred to triplicate flat bottomed wells of 96 well micro plates (Falcon Primeria). After incubating for 3 days under 10% $CO_2$ the wells were pulsed for 4 hours with 1 uCi of $^3$H-thymidine (Perkin Elmer/NEN). The cells were harvested on a multi well harvester apparatus (Brandel Scientific), and uptake of the isotope was quantitated on a liquid scintillation counter (Beckman).

To measure the proliferative response to allogeneic stimulator PBMNC, $1\times10^7$ cells/ml of allogenenic stimulator cells were treated with mitomycin C (Sigma) 33 ug/ml in R10 medium for 30 minutes at 37° C. Mitomycin C was removed by washing 2× with 30 ml of R10 medium. The experimental treated and control PBMNC as well as the allogeneic mitomycin C treated cells were adjusted to $1\times10^6$ cells/ml in R10 medium. The treated and control PBNMNC were transferred in 100 μL volumes to triplicate flat bottom wells (Falcon Primaria). After adding an equal volume of the mitomycin C allogeneic stimulators the plates were incubated for 5 days at 37° C. under 10% $CO_2$, and cell proliferation assessed by uptake of 1 uCi of $^3$H-thymidine.

Table 2B below shows that treated PBMNC were unable to proliferate in response to either PHA or allogeneic stimulator cells.

TABLE 2B

| Experiment No. | Untreated cells | | Treated cells | |
|---|---|---|---|---|
| | +PHA | −PHA | +PHA | −PHA |
| 1 | 42349 ± 3947 | 643 ± 31 | 1387 ± 86 | 1070 ± 187 |
| 2 | 108946 ± 989 | 396 ± 37 | 222 ± 56 | 225 ± 27 |
| 3 | 117373 ± 14215 | 589 ± 27 | 326 ± 4 | 336 ± 84 |
| Mean | 89556 | 543 | 645 | 544 |
| ±SD | 41099 | 130 | 644 | 459 |
| | +Stimulators | −Stimulators | +Stimulators | −Stimulators |
| 1 | 41598 ± 4697 | 5019 ± 3391 | 430 ± 73 | 450 ± 191 |
| 2 | 38089 ± 19733 | 6813 ± 1880 | 322 ± 137 | 349 ± 88 |
| 3 | 45652 ± 5515 | 596 ± 143 | 234 ± 43 | 251 ± 80 |
| Mean | 41780 | 4143 | 329 | 350 |
| ±SD | 3784 | 3200 | 98 | 100 |

2. C. The Ability of Treated or Untreated PBMNC to Stimulate Proliferation

While treatment with riboflavin and light appears to inhibit the proliferation of treated PBMNCs, there remains the possibility that although the treated donor cells themselves may not proliferate, they may act as stimulator cells to other responder immune cells in a transfusion recipient, causing the recipient's body to mount an immune response to the treated transfused cells, causing ultimate rejection of the cells. This was tested by measuring the ability of the treated and untreated PBMNC to stimulate the proliferation of allogeneic responder PBMNC.

The assay was set up as described in section 2 B. above. The experimental treated and control PBMNC as well as the allogeneic responder PBMNC were adjusted to $1\times10^6$ cells/ml in R10 medium. The treated and control PBMNC were transferred in 100 μL volumes to triplicate flat bottom wells (Falcon Primaria). After adding an equal volume of the allogeneic responder PBMNC the plates were incubated for 5 days at 37° C. under 10% $CO_2$, and cell proliferation assessed by uptake of 1 uCi of $^3$H-thymidine as for PHA (see above).

The results in Table 2C below show that the treated cells do not stimulate proliferation of allogeneic responder cells.

TABLE 2C

| Experiment No. | Untreated cells | | Treated cells | |
|---|---|---|---|---|
| | +Responder | −Responder | +Responder | −Responder |
| 1 | 55483 ± 3232 | 436 ± 126 | 548 ± 221 | 436 ± 126 |
| 2 | 50690 ± 750 | 3028 ± 3323 | 806 ± 619 | 3028 ± 3323 |
| 3 | 55295 ± 6149 | 412 ± 65 | 510 ± 90 | 412 ± 65 |
| Mean | 53823 | 1292 | 621 | 1292 |
| ±SD | 2714 | 1503 | 161 | 1503 |

EXAMPLE 3

While the results obtained using the in vitro assays above demonstrate that treatment with riboflavin and light inactivates the treated PBMNC, it remains important to confirm these results with an assay that measures the in vivo responsiveness of the treated or untreated PBMNC. One such assay is to measure xenogeneic GVHD responses in mice which have been transfused with human PBMNCs. These mice ($Rag^{-/-}\,\gamma c^{-/-}$ double knockout mice) lack T and B lymphocytes as well as natural killer (NK) cells, and previous studies have shown that the injection of human WBC into these mice results in xenogeneic GVHD that is characterized by xenoreactive T cells.

Characterization of Donor Cells

White blood cells were obtained from the leukocyte reduction chamber of a Trima® machine following platelet donation from 6 different human donors. The cells were separated into the mononuclear cell fraction using Ficoll-Hypaque discontinuous centrifugation and then placed in a platelet bag containing autologous plasma. Treated cells received treatment with riboflavin and light, while control cells received no treatment.

3. A. Induction and Clinical Observations of Xenogeneic GVHD Mice $Rag2^{-/-}\gamma c^{-/-}$ double knockout mice were obtained from Taconic (Germantown, N.Y.).

Injection of Cells

The recipient mice received 350 cGy irradiation the night before injection. The number of donor cells either treated or untreated containing $30\times10^6$ $CD3^+$ cells was determined and 3 mice were injected intraperitoneally with that number of cells per group. Each injected mouse was assigned a number. Mice receiving treated cells were given the prefix T, mice receiving untreated cells were given the prefix C.

Analysis of GVHD Response

Mice were weighed twice per week and observed regularly. Recipient mice that demonstrated a dramatic weight loss (usually >20%) and exhibited lethargy, hunched posture and ruffled fur were considered to have developed a GVHD response and were euthanized. Blood was collected by cardiac puncture using a heparinized syringe. In addition, the spleen, bone marrow from the femurs, liver and any intestinal lymphoid tissue that was observed was collected. The weight of the spleen was determined and then single cell suspensions were prepared from all organs by rubbing the organ on a screen. The liver mononuclear cell population was obtained from the liver cells by centrifuging the cells over a Ficoll-Hypaque discontinuous gradient and collecting the cells at the interface. The blood was centrifuged and the plasma collected and stored at −20° C. The buffy coat cells were collected and the red blood cells were lysed using RBC Lysis solution (Gentra, Minneapolis, Minn.). All mice that did not exhibit a GVHD response were euthanized by day 63 (designated as N/A in table below) and a similar analysis was conducted on all of these recipient mice as well.

Analysis of Cells

Cells were initially stained with PECy5 or PE anti-human CD45 or isotype control and then analyzed for the presence of human CD45+ cells in the organs of the transfused mice. CD45+ is a marker found on all leukocytes. The results are shown in Table 3A below.

TABLE 3A

| Mouse No. | Treatment | Death (day) | Spleen weight | Hct | % CD45 spleen | % CD45 blood | % CD45 bone marrow | % CD45 Intestinal lymphoid | % CD45 liver |
|---|---|---|---|---|---|---|---|---|---|
| | | | | | Donor 1 | | | | |
| T1 | Yes | N/A | 0.05 | 57 | 0.0 | 0.0 | 0.0 | ND | ND |
| T2 | Yes | N/A | 0.02 | 57 | 0.0 | 0.0 | 0.0 | ND | ND |
| T3 | Yes | N/A | 0.04 | 55 | 0.0 | 0.0 | 0.0 | ND | ND |
| C4 | No | 55 | 0.59 | 21 | 1.9 | 0.2 | 0.8 | 66.8 | 6.6 |
| C5 | No | N/A | 0.03 | 20 | 0.1 | 0.0 | 0.2 | ND | 0.01 |
| C6 | No | 57 | 0.79 | 23 | 3.0 | 0.3 | 0.6 | 48.4 | 3.3 |
| | | | | | Donor 3 | | | | |
| T7 | Yes | N/A | 0.04 | 55 | 0.0 | 0.0 | 0.0 | ND | ND |
| T8 | Yes | N/A | 0.20 | 48 | 0.0 | 0.0 | 0.0 | ND | ND |
| T9 | Yes | N/A | 0.18 | 50 | 0.0 | 0.0 | 0.0 | ND | ND |
| C10 | No | 43 | ND | 68 | 54.9 | 3.3 | 1.7 | 67.8 | 35.7 |
| C11 | No | 19 | ND | ND | 11.2 | ND | ND | ND | ND |
| C12 | No | 48 | 0.04 | 42 | 42.1 | 3.9 | 7.36 | 45.8 | 70.7 |
| | | | | | Donor 4 | | | | |
| T13 | Yes | N/A | 0.03 | 56 | 0.0 | 0.0 | 0.0 | ND | ND |
| T14 | Yes | N/A | 0.02 | 56 | 0.0 | 0.0 | 0.0 | ND | ND |
| T15 | Yes | N/A | 0.02 | 57 | 0.0 | 0.0 | 0.0 | ND | ND |
| C16 | No | 61 | 0.07 | 25 | 31.3 | 4.7 | 3.2 | 26.8 | 7.2 |
| C17 | No | 58 | 0.09 | 26 | 36.9 | 4.3 | 3.5 | 82.6 | 7.8 |
| C18 | No | 58 | 0.02 | 34 | 47.6 | 8.1 | 16.6 | 91.3 | ND |
| | | | | | Donor 5 | | | | |
| T19 | Yes | 37 | ND | ND | 0.0 | 0.0 | 0.0 | ND | ND |
| T20 | Yes | N/A | 0.11 | 52 | 0.0 | 0.0 | 0.0 | ND | ND |
| T21 | Yes | N/A | 0.19 | 53 | 0.0 | 0.0 | 0.0 | ND | ND |
| C22 | No | 42 | 0.12 | 6 | 15.5 | 16.7 | 3.7 | 91.0 | 19.1 |
| C23 | No | 42 | 0.30 | 6 | 4.7 | 7.6 | 1.1 | 44.5 | 14.9 |
| C24 | No | 51 | ND | ND | ND | ND | ND | ND | ND |
| | | | | | Donor 6 | | | | |
| T25 | Yes | N/A | 0.04 | 52 | 0.0 | 0.0 | 0.0 | ND | ND |
| T26 | Yes | N/A | 0.03 | 53 | 0.0 | 0.0 | 0.0 | ND | ND |
| T27 | Yes | N/A | 0.01 | 52 | 0.0 | 0.0 | 0.0 | ND | ND |
| C28 | No | 60 | 0.20 | 40 | 38.3 | 1.5 | 1.9 | 43.5 | 20.9 |
| C29 | No | 60 | 0.31 | 38 | 39.8 | 1.0 | 6.0 | 1.4 | 36.5 |
| C30 | No | 38 | 0.68 | 13 | 47.6 | 8.1 | 16.6 | 91.32 | ND |

Conclusions

The clinical evaluation of the mice found that one from 15 recipients per group injected with either untreated or treated cells died of unknown causes. No weight loss or human CD45+ cells were detected in the remaining 14 recipients injected with treated cells. These mice had an average spleen weight of 0.07±0.07 g and an average hematocrit of 53.8±2.8%. In contrast 12 of 14 recipients injected with untreated cells were euthanized because of GVHD symptoms including >20% loss of weight and hunched posture, ruffled fur and lethargy and 13 of 14 recipients had high levels of human cell chimenism. This recipient group had an average spleen weight of 0.27±0.27 g, which is significantly larger (p=0.0138) than that of the treated mice (p value<0.02), and an average hematocrit of 27.9±16.9%, which is also significantly lower than that of the treated mice (p value <0.02).

A summary of the results is shown in the following table:

|  | Total mice No. | No. of survivors at end of study | No. of dead during study GVHD | No. of dead during study non-GVHD | GVHD death rate | Body weight loss rate |
|---|---|---|---|---|---|---|
| Treated Group | 15 | 14 | 0 | 1 | 0/14 | 0/14 |
| Control Group | 15 | 2 | 12 | 1 | 12/14 | 13/14 |

3. B. Phenotypic and Functional Analysis of Chimeric Human Cells

If human CD45+ cells were detected and enough cells remained for further study, a second battery of staining was done in which the expression of leukocyte subpopulation markers including CD3 (all T cells), CD4 (T helper cells), CD8 (cytotoxic cells), CD14 (macrophages), CD19 (B cells), and CD56 (NK cells) was measured. The data shown in Table 3B below is expressed as % of total cells.

TABLE 3B

| Source of cells | Mouse No. | % CD3 | % CD4 | % CD8 | % CD56 | % CD19 | % CD14 |
|---|---|---|---|---|---|---|---|
| Donor 1 | | | | | | | |
| Spleen | C4 | 1.64 | 0.62 | 0.88 | 0.05 | 0.25 | 1.9 |
| Intestinal | C4 | 20.30 | 8.47 | 11.07 | | 75.36 | |
| Spleen | C6 | 0.81 | 0.54 | 0.57 | | 3.38 | |
| Intestinal | C6 | 8.63 | 6.09 | 1.99 | | 32.26 | |
| Donor 3 | | | | | | | |
| Blood | C10 | 1.24 | 0.3 | 1.16 | | 2.22 | |
| Spleen | C10 | 51.42 | 14.72 | 38.90 | | 6.26 | |
| Liver | C10 | 5.68 | 3.08 | 4.14 | | 25.90 | |
| BM | C10 | 1.98 | 0.58 | 0.58 | | 1.48 | |
| Intestinal | C10 | 6.06 | 3.24 | 6.04 | | 37.24 | |
| Blood | C12 | 1.23 | 0.22 | 1.14 | 7.5 | 3.82 | |
| Spleen | C12 | 33.07 | 6.52 | 24.16 | 6.09 | 18.03 | |
| Liver | C12 | 2.28 | 1.82 | 7.42 | | 24.86 | |
| BM | C12 | 3.32 | 0.68 | 3.19 | | 3.43 | |
| Intestinal | C12 | 6.52 | 1.85 | 4.86 | | 22.06 | |
| Donor 4 | | | | | | | |
| Spleen | C16 | 5.09 | 3.25 | 2.09 | | 28.21 | |
| BM | C16 | 0.40 | 0.34 | | | | |
| Intestinal | C16 | 12.28 | 3.52 | 1.06 | | 32.84 | |
| Blood | C17 | 0.90 | 0.28 | | | | |
| Spleen | C17 | 2.80 | 3.65 | 1.96 | | 14.05 | |
| Liver | C17 | 1.05 | 0.34 | | | | |
| BM | C17 | 0.97 | | 0.39 | | | |
| Intestinal | C17 | 4.57 | 3.72 | 1.68 | | 7.74 | |

TABLE 3B-continued

| Source of cells | Mouse No. | % CD3 | % CD4 | % CD8 | % CD56 | % CD19 | % CD14 |
|---|---|---|---|---|---|---|---|
| Blood | C18 | 2.71 | 0.32 | 0.23 | | | |
| BM | C18 | 1.00 | 0.59 | 0.48 | | 1.48 | |
| Intestinal | C18 | 3.59 | 0.85 | 0.85 | | 2.15 | |
| Donor 5 | | | | | | | |
| Blood | C22 | 5.84 | 4.54 | 1.25 | 2.33 | 0.71 | |
| Spleen | C22 | 14.62 | 11.25 | 4.67 | | | |
| Liver | C22 | 18.94 | 17.12 | 2.52 | | | |
| BM | C22 | 2.74 | 2.98 | 1.50 | | | |
| Intestinal | C22 | 43.25 | 40.27 | 16.07 | 5.21 | 71.2 | |
| Blood | C23 | 7.76 | 5.74 | 1.31 | | | |
| Spleen | C23 | 4.55 | 2.96 | 2.41 | | | |
| Liver | C23 | 13.08 | 11.30 | 2.24 | | | |
| Donor 6 | | | | | | | |
| Blood | C28 | 2.8 | 0.36 | 1.98 | | 2.42 | |
| Spleen | C28 | 46.6 | 7.9 | 39.9 | | 11.0 | |
| Liver | C28 | 14.46 | 1.50 | 10.86 | | 19.9 | |
| Intestinal | C28 | 31.38 | 8.54 | 18.26 | | 25.22 | |
| Blood | C29 | 9.23 | 1.79 | 5.84 | | | |
| Spleen | C29 | 19.68 | 5.86 | 11.96 | | | |
| Liver | C29 | 3.56 | 3.08 | 0.32 | | 29.3 | |
| BM | C29 | 6.70 | 2.22 | 5.76 | | | |
| Blood | C30 | 8.02 | 6.46 | 0.98 | | | |
| Spleen | C30 | 42.96 | 29.84 | 27.2 | | | |
| BM | C30 | 13.96 | 9.9 | 6.08 | | | |
| Intestinal | C30 | 22.84 | 14.24 | 10.52 | | 10.22 | |

Results

When examined in a donor by donor fashion, the results indicate that the makeup of donor cells trans fused can influence the type of cells that are present in different lymphoid organs and in which organs they will be found. CD3+ cells were found in varying numbers in the different lymphoid compartments and CD19+ cells were primarily found in the intestinal lymphoid tissue and in the liver. In contrast to these findings, no macrophages were found and only a limited number of CD56+ cells in a few mice.

3. C. The Level of Cytokines in the Plasma of Rag2$^{-/-}$γc$^{-/-}$ Recipients of Treated and Untreated White Blood Cells Plasma of recipient mice was collected when the mice were euthanized either because they were demonstrating symptoms of GVHD or because the experiment was terminated. The levels of cytokines associated with inflammation and acute phase response were measured using the CBA cytometric bead assay kits available from BD Biosciences. The measurement of cytokines associated with the inflammation response is another approach to determine if recipient mice develop an acute phase response to transplanted human cells and also helps define the nature of the xenogeneic GVHD response.

Results are shown in Table 3C below. As can be seen, human cells treated with riboflavin and light do not cause a significant production of inflammatory cytokines.

TABLE 3C

| Mouse No. | Treatment | Cytokine concentration in plasma (pg/ml) | | | |
|---|---|---|---|---|---|
| | | IL-1β | IL-6 | IL-8 | IL-12p70 |
| Donor 1 | | | | | |
| T1 | Yes | 0.1 | 0.1 | 0.1 | 0.1 |
| T2 | Yes | 32.5 | 0.1 | 2.5 | 4.8 |

TABLE 3C-continued

| Mouse No. | Treatment | Cytokine concentration in plasma (pg/ml) | | | |
|---|---|---|---|---|---|
| | | IL-1β | IL-6 | IL-8 | IL-12p70 |
| T3 | Yes | 0.1 | 0.1 | 1.5 | 0.1 |
| C5 | No | 0.1 | 0.1 | 3.2 | 4.9 |
| C4 | No | 0.1 | 6.3 | 28.4 | 8.7 |
| C6 | No | 0.1 | 390.6 | 104 | 158.8 |
| Donor 3 | | | | | |
| T7 | Yes | 41.2 | 2.5 | 4.3 | 7.3 |
| T8 | Yes | 22.6 | 0.1 | 4 | 7.3 |
| T9 | Yes | 0.1 | 0.1 | 2.9 | 5 |
| C10 | No | 205.5 | 8.0 | 236.2 | 78.9 |
| C12 | No | 396.8 | 13.2 | 189.6 | 149.6 |
| Donor 4 | | | | | |
| T13 | Yes | 8.4 | 0.1 | 3.3 | 6.2 |
| T14 | Yes | 0.1 | 0.1 | 2.7 | 6.3 |
| T15 | Yes | 12.9 | 0.1 | 2.2 | 4.8 |
| C16 | No | 0.1 | 300 | 105 | 500 |
| C17 | No | 0.1 | 162.6 | 22.6 | 17.4 |
| C18 | No | 40 | 110 | 100 | 11 |
| Donor 5 | | | | | |
| T20 | Yes | 8.4 | 0.1 | 3.2 | 5.6 |
| T21 | Yes | 33.9 | 0.1 | 3.7 | 5.7 |
| C22 | No | 0.1 | 0.1 | 3.8 | 4.8 |
| C23 | No | 0.1 | 0.1 | 4.1 | 4.3 |
| Donor 6 | | | | | |
| T25 | Yes | 0.1 | 0.1 | 2 | 3.4 |
| T26 | Yes | 0.1 | 0.1 | 2.6 | 2.8 |
| T27 | Yes | 21.3 | 2.2 | 4.4 | 8.8 |
| C28 | No | 65 | 60 | 80 | 11 |
| C29 | No | 0.1 | 4.2 | 3.9 | 4.3 |
| C30 | No | 0.1 | 0.1 | 3.8 | 3.5 |

3. D. The Level of Human Immunoglobulins in the Plasma of Rag2$^{-/-}$γc$^{-/-}$ recipients of Untreated Control and Treated White Blood Cells Another measure of human cell chimerism is to determine the level of human IgG and IgM present in the plasma of the recipient mice using an ELISA assay. IgG and IgM are antibodies produced by B cells in response to an antigen. The results shown in Table 3D below indicate that no human IgG (0.10±0.24 ng/ml) or IgM (0.27±0.68 ng/ml) was detected in the plasma of mice injected with treated cells. High levels of IgG (5980.8±2780.8 ng/ml) or IgM (1389.6±845.3 ng/ml) were detected in the plasma of all recipients in which human cell chimerism was detected (these mice received untreated cells).

In vitro studies showed that treatment with riboflavin and light abolished the functional activity of human WBC cells. Consistent with these findings, treated human WBCs did not appear to generate a xenogeneic GVHD response in vivo following injection of these cells into immunodeficient Rag2$^{-/-}$γc$^{-/-}$ mice recipients. The lack of a xenogeneic GVHD response in the recipient mice also correlated with a lack of human cell chimerism as measured by immunophenotyping. The plasmas of these recipient mice were also found to lack human cytokines or immunoglobulins. These findings indicate that blood cells treated with riboflavin and light are unable to respond in vitro and in vivo and therefore should not induce TA-GVHD in a transfusion recipient.

EXAMPLE 4

This study evaluated the ability of treatment with riboflavin and light to modify the immune response to allogeneic solid organ transplants in rats.

Over a 10 week period, Lewis rats received 8 transfusions (shown by the small arrows in FIGS. 4 and 5) of untreated or treated platelet products containing leukocytes from DA rats. A third group of animals received saline injections. Antibody levels (IgG, IgM) were monitored weekly. At the end of the 10 week period (shown by the large arrow in FIGS. 4 and 5), the transfused animals underwent allogeneic heart transplants with hearts from DA rats to assess the effect pre-transplantation transfusions of platelets with riboflavin and light had on pre-sensitization and transplant rejection.

Figure 4:
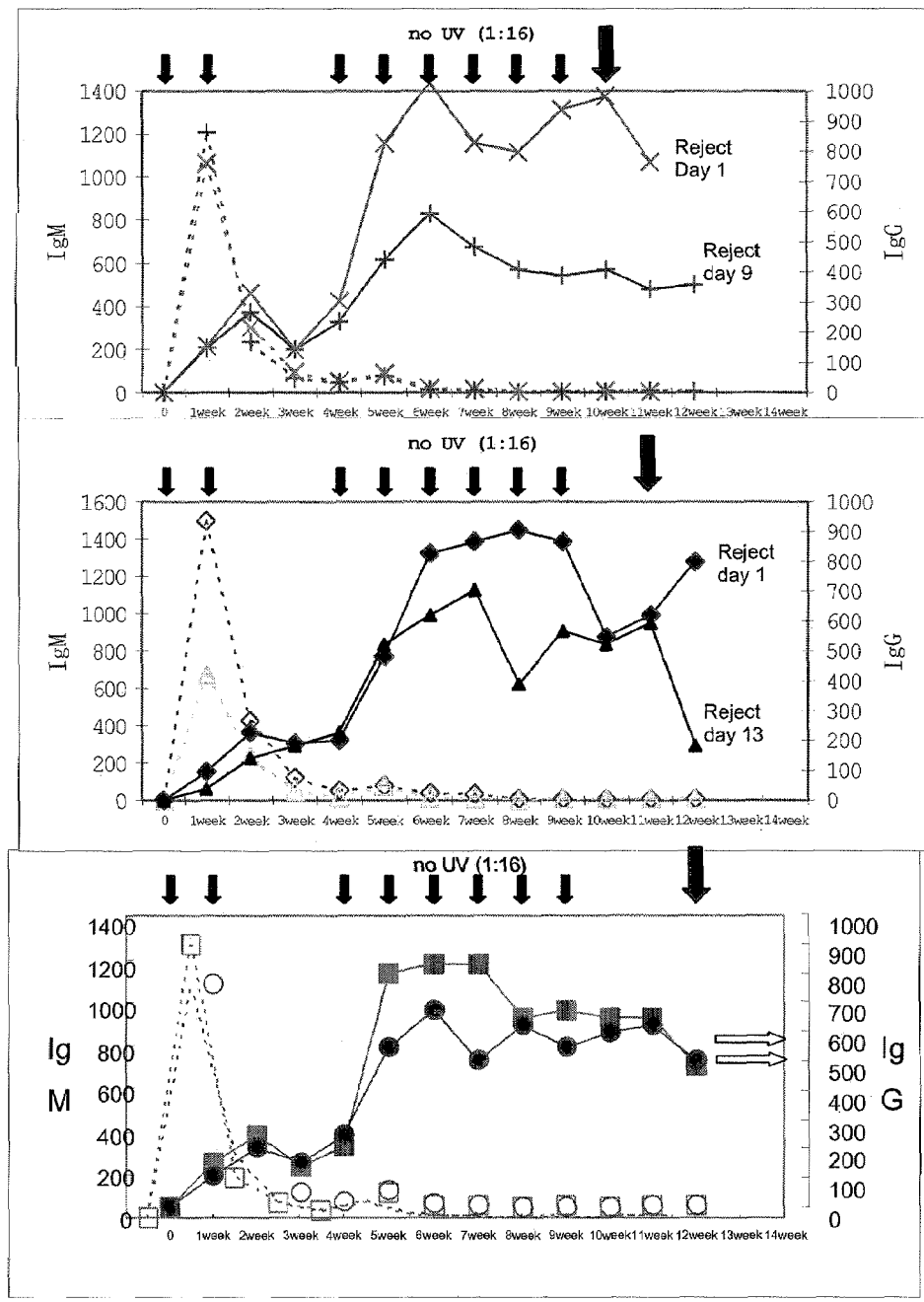
FIG. 4 is a graph measuring IgG and IgM production by rats transfused with untreated allogeneic platelets for 10 weeks before receiving an allogeneic heart transplant.
Figure 5:
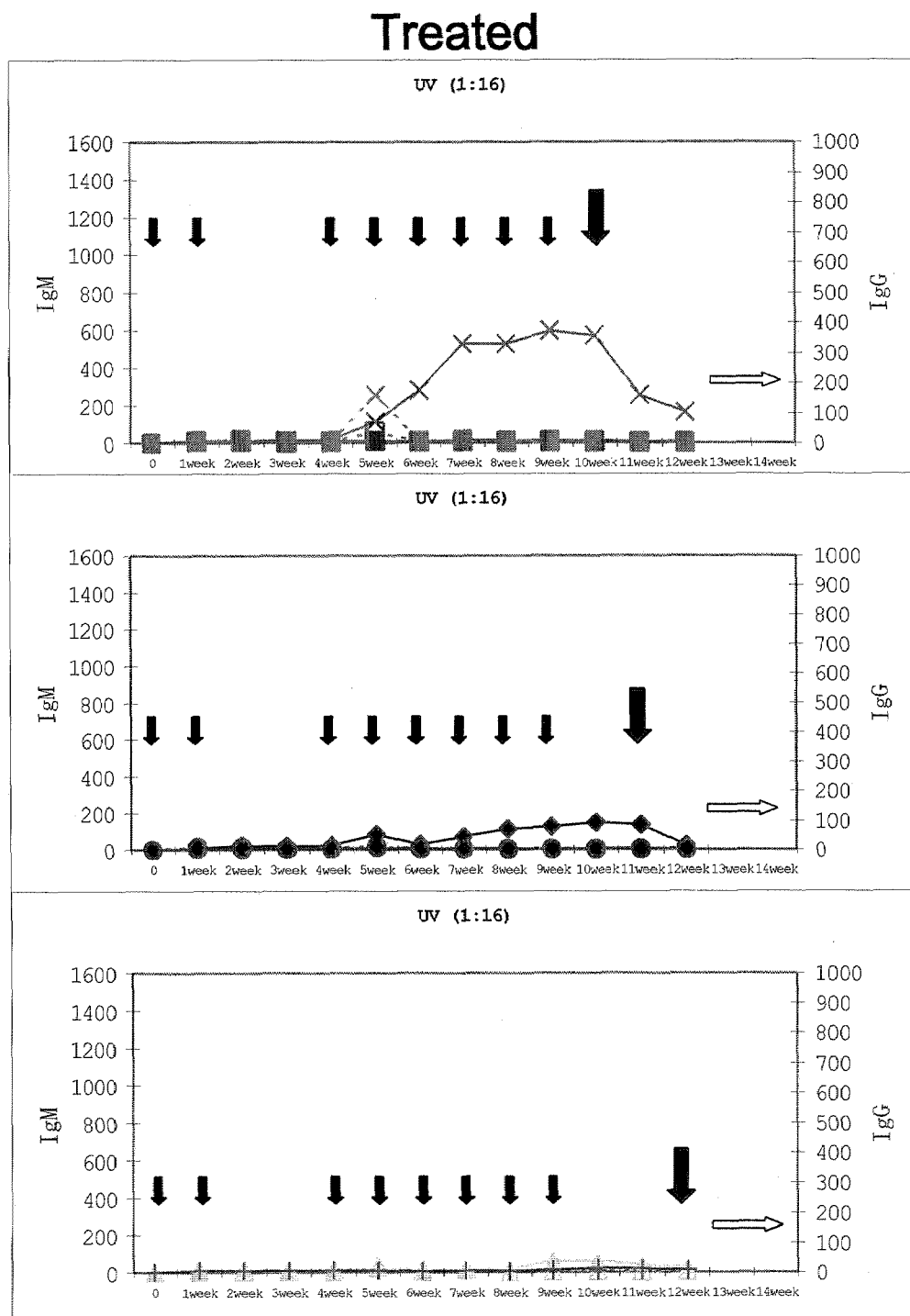
FIG. 5 is a graph measuring IgG and IgM production by rats transfused with treated allogeneic platelets for 10 weeks before receiving an allogeneic heart transplant.

As can be seen in FIG. 5, the IgM and IgG response in rats that received treated platelets was almost completely abolished compared to animals that received untreated platelets (FIG. 4). In preliminary experiments, (not shown) animals that mounted an IgG response also rejected the subsequent heart transplant.

In summary, treatment with riboflavin and light prevented the development of an Ig response in transplanted animals. This inhibition of an Ig response, in particular IgG, shows that pre-transfusion of a solid organ recipient with platelets treated with riboflavin and light helps to prevent alloimmunization to the transplanted allogeneic organ. The lack of rejection of the allogeneic heart transplant in the absence of an IgG response indicates that the pre-treatment may be effective in preventing alloimmune refractoriness to platelets and pre-sensitization to transplants.

TABLE 3D

| | Mice No. | | | | | | | | | | | | | | |
|---|---|---|---|---|---|---|---|---|---|---|---|---|---|---|---|
| | T1 | T2 | T3 | T7 | T8 | T9 | T13 | T14 | T15 | T19 | T20 | T21 | T25 | T26 | T27 |
| IgG (ng/ml) | 0 | 0 | 0 | 0 | 0 | 0 | 0.2 | 0 | 0 | ND | 0 | 0 | 0 | 0 | 0.9 |
| IgM (ng/ml) | 0 | 0 | 0 | 0 | 0.1 | 0 | 0 | 0 | 0 | ND | 0 | 2.1 | 0 | 2.1 | 0 |

| | Mice No. | | | | | | | | | | | | | |
|---|---|---|---|---|---|---|---|---|---|---|---|---|---|---|
| | C4 | C5 | C6 | C10 | C11 | C12 | C16 | C17 | C18 | C22 | C23 | C24 | C28 | C29 | C30 |
| IgG (ng/ml) | 5682 | 0 | 6134 | 4241 | ND | 4102 | 9087 | 10202 | 7283 | 8973 | 7034 | ND | 3478 | 4221 | 7314 |
| IgM (ng/ml) | 2189 | 0 | 1070 | 1383 | ND | 631 | 685 | 1500 | 800 | 2853 | 1676 | ND | 809 | 1746 | 2724 |

The invention claimed is:

1. A process for reducing transfusion related complications in a human recipient due to human donor cells that may be present in an allogeneic blood transfusion comprising the steps of:
    adding to the blood to be transfused a photosensitizer consisting essentially of riboflavin at a concentration of 50 µM;
    irradiating the blood and riboflavin with light at a wavelength between 290-370 nm for around 8 minutes to reduce transfusion related complications in the recipient caused by the donor cells;
        wherein the transfusion related complications are alloimmunization, Transfusion Associated Graft vs. Host Disease (TA-GvHD) or microchimerism;
    transfusing the irradiated blood into a recipient; and
    reducing transfusion related complications in the recipient.

2. The process of claim 1 wherein the blood to be transfused is whole blood.

3. The process of claim 1 wherein the blood to be transfused is platelets.

4. The process of claim 1 wherein the donor cells causing transfusion related complications comprise white blood cells.

5. The process of claim 1 wherein the donor cells causing transfusion related complications comprise platelets.

6. The process of claim 1 wherein the step of reducing transfusion related complications further comprises reducing alloimmunization by reducing activation of the donor cells in the recipient.

7. The process of claim 1 wherein the step of reducing transfusion related complications further comprises reducing alloimmunization by reducing proliferation of the donor cells in the recipient.

8. The process of claim 1 wherein the step of reducing transfusion related complications further comprises reducing alloimmunization by reducing production of cytokines by the donor cells in the recipient.

9. The process of claim 1 wherein the step of reducing transfusion related complications further comprises reducing microchimerism by reducing production of antibodies by the donor cells in the recipient.

* * * * *